United States Patent
Stanglmeier et al.

(10) Patent No.: US 9,525,280 B2
(45) Date of Patent: Dec. 20, 2016

(54) PLUG FOR SEALING A HOUSING OF AN EXHAUST GAS SENSOR, EXHAUST GAS SENSOR AND MANUFACTURE OF AN EXHAUST GAS SENSOR

(71) Applicant: Robert Bosch GmbH, Stuttgart (DE)

(72) Inventors: Frank Stanglmeier, Eberdingen-Hochdorf (DE); Jens Schneider, Leonberg (DE); Bernd Rattay, Ditzingen (DE)

(73) Assignee: Robert Bosch GmbH, Stuttgart (DE)

( * ) Notice: Subject to any disclaimer, the term of this patent is extended or adjusted under 35 U.S.C. 154(b) by 185 days.

(21) Appl. No.: 14/376,936

(22) PCT Filed: Jan. 4, 2013

(86) PCT No.: PCT/EP2013/050115
§ 371 (c)(1),
(2) Date: Aug. 6, 2014

(87) PCT Pub. No.: WO2013/117357
PCT Pub. Date: Aug. 15, 2013

(65) Prior Publication Data
US 2015/0001813 A1 Jan. 1, 2015

(30) Foreign Application Priority Data
Feb. 9, 2012 (DE) .......... 10 2012 201 903

(51) Int. Cl.
*H02G 15/013* (2006.01)
*B29C 65/02* (2006.01)
(Continued)

(52) U.S. Cl.
CPC ............ *H02G 15/013* (2013.01); *B29C 65/02* (2013.01); *B29C 65/48* (2013.01); *F01N 11/00* (2013.01);
(Continued)

(58) Field of Classification Search
CPC ... G01N 27/4078; H02G 15/013; F01N 11/00; F01N 2560/02; B29C 65/02; B29C 65/48; B29K 2027/12; B29K 2027/16; B29K 2027/18
(Continued)

(56) References Cited

U.S. PATENT DOCUMENTS 5,949,023 A * 9/1999 Weyl .................. G01N 27/4062
174/652
6,018,982 A * 2/2000 Friese .................. G01N 27/407
204/410
(Continued)

FOREIGN PATENT DOCUMENTS

DE 40 34 072 4/1992
DE 196 11 572 9/1997
(Continued)

*Primary Examiner* — Daniel S Larkin
(74) *Attorney, Agent, or Firm* — Norton Rose Fulbright US LLP; Gerard Messina (57) ABSTRACT

A plug for sealing a housing of an exhaust gas sensor, the plug having at least one axial through-channel for leading through a connecting cable, the plug having a main body which includes polytetrafluoroethylene, the plug further including at least one outer seal which is situated on the plug radially on the outside, the outer seal including at least one perfluoroalkoxy polymer or tetrafluoroethylene-perfluoropropylene or polychlorotrifluoroethylene or polyvinylidene fluoride.

16 Claims, 5 Drawing Sheets (51) Int. Cl.
*B29C 65/48* (2006.01)
*F16J 15/02* (2006.01)
*F01N 11/00* (2006.01)
*G01N 27/407* (2006.01)
*B29K 27/12* (2006.01)
*B29K 27/00* (2006.01)
*B29K 27/18* (2006.01)

(52) U.S. Cl.
CPC ......... *F16J 15/022* (2013.01); *G01N 27/4078* (2013.01); *B29K 2027/12* (2013.01); *B29K 2027/16* (2013.01); *B29K 2027/18* (2013.01); *F01N 2560/02* (2013.01)

(58) Field of Classification Search
USPC .......................................................... 73/23.31
See application file for complete search history.

(56) References Cited

U.S. PATENT DOCUMENTS

| | | | |
|---|---|---|---|
| 6,672,132 B1* | 1/2004 | Weyl | G01N 27/407 73/23.31 |
| 2007/0033986 A1* | 2/2007 | Wild | G01N 37/00 73/31.05 |

FOREIGN PATENT DOCUMENTS

| | | |
|---|---|---|
| DE | 196 31 501 | 2/1998 |
| DE | 10 2005 020973 | 11/2006 |
| JP | 55159369 A | 12/1980 |
| JP | 59200649 A | 11/1984 |
| JP | 04285849 A | 10/1992 |
| JP | 11190717 A | 7/1999 |
| JP | 2001 103645 | 4/2001 |
| JP | 2001 242128 | 9/2001 |

* cited by examiner

PLUG FOR SEALING A HOUSING OF AN EXHAUST GAS SENSOR, EXHAUST GAS SENSOR AND MANUFACTURE OF AN EXHAUST GAS SENSOR

FIELD OF THE INVENTION

The present invention is directed to an exhaust gas sensor. Such exhaust gas sensors include a housing in which, for example, a ceramic, electrochemically operating sensor element is situated. Such exhaust gas sensors moreover include a plug, which seals the housing and through which at least one connecting cable is led out of the housing, or into the housing.

BACKGROUND INFORMATION

On the one hand, this plug and the cooperation of the plug with the housing are required to have great tightness. The great tightness effectively and permanently suppresses the penetration of harmful liquids and gases, for example those that trigger corrosion, into the interior of the exhaust gas sensor. To achieve the tightness, the plug is in particular required to have sufficient elasticity. Due to the high exhaust gas temperatures to which the exhaust gas sensor is exposed, on the other hand only materials which have a corresponding high temperature resistance may be used for the stopper.

German patent document DE 10 2005 020 793 A1 refers to providing a plug made of polytetrafluoroethylene, also known as PTFE, for closing the housing of an exhaust gas sensor. Force-fit sealing between the housing and a cable lead-through of the exhaust gas sensor with the aid of a tube made of fluorine-containing plastic is provided.

SUMMARY OF THE INVENTION

According to the present invention, a plug as recited in Claim 1 and an exhaust gas sensor as described herein including such a plug are provided.

According to the present invention, the plug has a main body which includes polytetrafluoroethylene (PTFE). Although the term "main body" in connection with the present invention shall not be understood in an exceedingly limiting manner, it still may be that the main body of the plug has the shape or basic shape of a straight circular cylinder, or is similar to the same, or is based on the same. For example, proceeding from the shape or the basic shape, chamfers, roundings and/or the like may be carried out and/or deformations of a plastic and/or elastic nature, for example, may be carried out.

Polytetrafluoroethylene (PTFE) shall be understood here to mean in particular the chemical substance with the formula —CF2-CF2- n.

Since according to the present invention the main body of the plug includes polytetrafluoroethylene (PTFE), i.e., a material having outstanding temperature resistance, it is advantageous when the main body predominantly contributes to the mass and/or to the volume of the plug. In particular, it may be advantageous when the main body accounts for at least 80% or at least 85%, which may be even at least 90% or at least 95%, of the mass of the plug. In addition or as an alternative, it may also be advantageous when the main body accounts for at least 65% or at least 72%, which may be even at least 79% or at least 86%, of the volume of the plug.

Although the main body may also have only a certain content of polytetrafluoroethylene (PTFE) with respect to a spatial part and/or with respect to its chemical composition, it still may be that at least 95% or all of the main body is made of polytetrafluoroethylene (PTFE) and/or that the main body is made of polytetrafluoroethylene (PTFE).

According to the present invention, the plug has at least one axial through-channel for leading through at least one connecting cable. For example, based on a cylindrical or cylinder-like shape or basic shape of the main body, an axial through-channel shall be understood to mean that the through-channel penetrates the two opposing end faces of the plug and/or that the through-channel does not penetrate the, in particular radially outer, lateral surface of the plug. Although the present invention is not limited to this, it still may be that the through-channel extends in parallel to an axis of symmetry of the main body or that an axis of symmetry of the main body even coincides with an axis of symmetry of the through-channel. An arrangement of multiple, in particular two, three, four, five or six, through-channels is also possible, these may also be symmetrically situated around an axis of symmetry of the main body. Although the arrangement of exactly one connecting cable per through-channel may be used, it is generally also possible to provide multiple connecting cables in one through-channel or to provide a combination of connecting cables which is bonded and/or welded, for example, and includes multiple connecting cables.

According to the present invention, the plug includes an outer seal, which is situated radially on the outside on the plug or on the main body. This outer seal may be suitable for closing, in particular sealing, a gap remaining between the main body of the plug and a housing of an exhaust gas sensor. Although it is possible and also may be the case that the outer seal covers, in particular predominantly or completely covers, the outer contour of the main body, it is also possible and may be the case that the outer seal is situated only in places radially on the outside on the plug or on the main body, i.e., portions of the outer contour of the main body remain open and are suitable for being situated directly opposite the housing of an exhaust gas sensor.

The present invention is based on the finding that the selection of the material of the outer seal is particularly significant to achieve an improved sealing action in the area of the outer seal. In particular, it is recognized that, while the main body has a high temperature resistance due to the material which it includes or of which it is even made, polytetrafluoroethylene (PTFE), it has elastic properties only to a lesser degree and is therefore insufficiently suited for transferring a force or a state of stress. A sealing action based on a force fit is thus achievable only with difficulty or not at all. Based on this finding, it was moreover recognized that the search for suitable materials for the outer seal must be focused on such materials which are suitable for integrally joining with polytetrafluoroethylene (PTFE), i.e., which are in particular suitable for wetting the substance polytetrafluoroethylene (PTFE).

According to the present invention and based on the above-mentioned findings, the substances perfluoroalkoxy (PFA) polymer and tetrafluoroethylene-perfluoropropylene (FEP) were identified as being suitable in analyses conducted by the applicant. The substances polychlorotrifluoroethylene (PCTFE) and polyvinylidene fluoride (PVDF) were also identified as being suitable. However, due to their slightly lower temperature resistance compared to perfluoroalkoxy (PFA) polymer and tetrafluoroethylene-perfluoropropylene (FEP), the substances polychlorotrifluoroethylene (PCTFE) and polyvinylidene fluoride (PVDF) should only be provided for use at lower usage temperatures (for example for usage temperatures below 210° C.). The use of perfluoroalkoxy (PFA) polymer and/or tetrafluoroethylene-perfluoropropylene (FEP) is the approach that may be used, in particular for high usage temperatures (for example for usage temperatures of up to 280° C. or even up to 305° C.)

Although the outer seal may be made of perfluoroalkoxy (PFA) polymer or tetrafluoroethylene-perfluoropropylene (FEP) or polychlorotrifluoroethylene (PCTFE) or polyvinylidene fluoride (PVDF) or a mixture of these substances, or that at least 95% or all of it is made of perfluoroalkoxy (PFA) polymer or tetrafluoroethylene-perfluoropropylene (FEP) or polychlorotrifluoroethylene (PCTFE) or polyvinylidene fluoride (PVDF) or a mixture of these substances, the present invention generally also covers seals in which only a portion is made of these substances, or which are made of a material having a content, in particular a predominant content, of perfluoroalkoxy (PFA) polymer and/or tetrafluoroethylene-perfluoropropylene (FEP) and/or polychlorotrifluoroethylene (PCTFE) and/or polyvinylidene fluoride (PVDF).

Tetrafluoroethylene-perfluoropropylene (FEP) shall be understood to mean in particular the chemical substance with the formula —CF2-CF2-CF(CF3)-CF2- n. Tetrafluoroethylene-perfluoropropylene (FEP) shall be understood to mean in particular chemical substances which may be produced by polymerizing mixtures of the monomer tetrafluoroethylene (TFE) with a content of the monomer hexafluoropropylene (HFP) different from zero, in particular significantly different from zero.

Perfluoroalkoxy (PFA) polymers shall be understood to mean in particular chemical substances which may be produced by polymerizing mixtures of the monomer tetrafluoroethylene (TFE) with a content of the monomer perfluoropropyl vinyl ether (PPVE) different from zero, in particular significantly different from zero. Perfluoroalkoxy (PFA) polymers shall be understood to mean in particular chemical substances with the formula —CF2-CF2-CF (OR)—CF2- n, the side chain OR being at least one alkoxy group. In particular, fully fluorinated polymers having at least one alkoxy side chain are involved. Perfluoroalkoxy (PFA) polymers are in particular chemical substances which are thermoplastically processable, are able to wet ceramic, oxidic, glass and/or metal surfaces and/or are fusible with polytetrafluoroethylene (PTFE). The present invention covers in particular different PFA grades and/or mixtures of different PFA grades, so-called PFA polyblends. The applicant has made particularly positive experiences in connection with the present invention with the use of PFA polyblends whose melting range is between 260° C. and 320° C., in particular from 260° C. to 320° C. Polymers having a molar mass of $3*10^5$ to $3*^10^6$ g/mole may be used.

Polychlorotrifluoroethylene (PCTFE) shall be understood to mean in. particular the chemical substance with the formula —CFCl—CF2- n.

Polyvinylidene fluoride (PVDF) shall be understood to mean in particular the chemical substance with the formula —CH2-CF2- n.

While the temperature stability of the materials provided for the outer seal, in particular perfluoroalkoxy (PFA) polymer and tetrafluoroethylene-perfluoropropylene (FEP) and polychlorotrifluoroethylene (PCTFE) and polyvinylidene fluoride (PVDF), is relatively high, it is nonetheless noticeably below the temperature stability of the material polytetrafluoroethylene (PTFE) provided for the main body. For this reason, it may be advantageous when the outer seal and/or the material of which the outer seal is made contribute/contributes only to a lesser degree to the mass and/or to the volume of the plug. In particular, it may be advantageous when the outer seal and/or the material of which the outer seal is made accounts/account for no more than 20% or no more than 15%, which may be even no more than 10% or no more than 5%, of the mass of the plug. In addition or as an alternative, it may also be advantageous when the outer seal and/or the material of which the outer seal is made accounts/account for no more than 20% or no more than 15%, which may be even no more than 10% or no more than 5%, of the volume of the plug. The described measures optimize the overall temperature stability of the plug.

In particular, it is possible for the outer seal to be situated on the main body in the form of an outwardly directed layer, in particular layer thicknesses of at least 10 µm, which may be at least 50 µm, having been successfully employed, since a formation of the outer sealing layer is thus ensured with high process reliability. A layer thickness which should not be exceeded is 1 mm, which may be 250 µm. In particularly temperature-critical applications, a layer thickness between 50 µm and 150 µm may also be used, in particular when a fluctuation in the actual layer thickness of 20%, which may be of 15%, is not exceeded.

Generally it is possible and covered by the present invention that an integral joint between the outer seal and the main body is not yet produced, or is not yet completely produced, at the factory and may be formed, or may be completely formed, in particular during the operation of the sensor, for example by self-heating of the sensor and/or as a result of hot exhaust gas striking the exhaust gas sensor. In one advantageous specific embodiment of the present invention, however, the creation of this integral joint is already integrated into the manufacturing process, so that then a plug or an exhaust gas sensor is present in which the main body is entirely or partially integrally joined with the outer seal and in which an optimized sealing action already exists at the beginning of the intended operation of the sensor.

An integral joint is a joint in which a cohesion of the joining partners takes place by forces acting at the molecular level, as is defined in particular also in VDI Guideline 2232-2004-01. Examples of integral joints are welded joints, glued joints, melted joints and the like. The integral joint may be in particular a direct integral joint between two joining partners, in which a direct interaction takes place between the two joining partners at the molecular level. On the other hand, the integral joint may in particular also be an indirect integral joint in which the two joining partners are not directly integrally joined with each other, but are indirectly integrally joined in each case with at least one third joining partner, and in the case of multiple third joining partners, all these third joining partners are (indirectly or directly) integrally joined with each other.

The plug according to the present invention has an, in particular axial, through-channel for leading through a connecting cable. This means that the through-channel is generally configured in such a way that a connecting cable may be led through the plug, which may be may be led through the plug out of the interior of the housing into an area situated outside the housing.

One refinement of the present invention provides for the plug to include a connecting cable which is led through the plug, which may be led through the plug out of the interior of the housing into an area situated outside the housing.

Presently, an exhaust gas sensor shall be understood to mean in particular a lambda sensor for use in the exhaust tract of an internal combustion engine; however, it may also be other sensors, for example a temperature sensor or an NOx or soot particle sensor or the like. In particular, the present invention covers all sensors which are suitable for permanent use at high temperatures and/or in corrosive surroundings, and such sensors in which an electrical connecting line, for example, is to be led out of a housing to be sealed, in particular at comparatively high ambient temperatures.

The provision of the measures according to the present invention may result in comparatively great tightness of the housing of the exhaust gas sensor on the connection side, for example a helium tightness of less than $10^{-3}$ mbar*l/s or $10^{-4}$ mbar*l/s, which may be even a helium tightness of less than $10^{-5}$ mbar*l/s or $10^{-6}$ mbar*l/s. On the other hand, the terms "seal," "sealed" and the like also shall not be interpreted too narrowly, so that in particular also only a macroscopic closure may be covered. A potentially remaining leak through the interior of a tubular insulation of the connecting cable or of the connecting cables is presently disregarded since this leak may be sealed elsewhere, at a connector connected to the connecting cable and to the connecting cables, for example. It may also be provided that such a leak is dissipated through the connecting cable, or through the connecting cables, into a non-critical area, for example a colder and less exposed area of a motor vehicle. While absolute or hermetic tightness (in particular a helium tightness of less than $10^{-10}$ mbar*l/s) is generally possible, it is equally as cost-prohibitive, with the exception of special applications.

To achieve comparatively great tightness of the housing, it particularly may be that the housing of the exhaust gas sensor is integrally joined with the outer seal.

Refinements of the present invention result by applying the basic idea of sealing the main body of the plug with respect to the housing of the exhaust gas sensor by providing the outer seal according to the present invention to sealing the main body of the plug with respect to the connecting line.

For example, it may be provided as one refinement that a seal is situated at least in places between the main body of the plug and the through-channel, the seal including at least one perfluoroalkoxy (PFA) polymer or a tetrafluoroethylene-perfluoropropylene (FEP) or a polychlorotrifluoroethylene (PCTFE) or a polyvinylidene fluoride (PVDF). In addition, the main body may be integrally joined with the seal. In addition or as an alternative, the seal may be situated on the main body in the form of a layer facing the through-channel, which may have a layer thickness of 10 μm to 1 mm, particularly may have a layer thickness of 50 μm to 250 μm.

In this way it may additionally or alternatively be provided that a connecting cable of the exhaust gas sensor is integrally joined with the seal. In addition or as an alternative, it may be provided that the connecting cable includes an electrical conductor surrounded by an insulation which in particular includes a fluoropolymer, for example polytetrafluoroethylene, or is made of polytetrafluoroethylene (PTFE), in particular is made entirely, predominantly or partially of polytetrafluoroethylene (PTFE). To optimize the tightness and the temperature resistance, it particularly may be when the insulation of the connecting cable is made of the same material as the main body of the plug, for example of polytetrafluoroethylene (PTFE).

The electrical conductor of the connecting cable is advantageously provided by Cu and/or Cu-steel strands.

In particular, it may be provided that the same material is provided for the outer seal and for the seal, i.e., in particular a material having the same chemical composition. The layer thicknesses provided for the seal and for the outer seal may also agree with each other.

To achieve comparatively great tightness of the housing, it particularly may be that the connecting cable, the plug and the housing are integrally joined with each other, i.e., in particular an integral bond is implemented between the housing and the plug, and a bond is implemented between the plug and the connecting cable, in particular between the plug and an insulation of the connecting cable. In particular, overall an integral seal of the connection-side end of the housing of the exhaust gas sensor is implemented.

Methods according to the present invention for manufacturing a plug, in particular a plug according to the present invention, and/or an exhaust gas sensor, in particular an exhaust gas sensor according to the present invention, provide that a main body which includes polytetrafluoroethylene (PTFE), in particular is made of polytetrafluoroethylene (PTFE), is provided. It is furthermore provided that an outer sealing material which includes at least one perfluoroalkoxy (PFA) polymer or a tetrafluoroethylene-perfluoropropylene (FEP) or a polychlorotrifluoroethylene (PCTFE) or a polyvinylidene fluoride (PVDF) is provided.

The outer sealing material may be in particular at least one tube, in particular a tube which is pushed, pulled or rolled onto the main body. The length of the tube in the axial direction may be greater than half its diameter, or greater than its diameter. Tubes may be used having a wall thickness from 10 μm to 1 mm, particularly having a wall thickness from 50 μm to 250 μm.

On the other hand, the outer sealing material may also be at least one film, in particular a film which is wound onto or around the main body. Films having a wall thickness from 10 μm to 1 mm may be used, particularly having a wall thickness from 50 μm to 250 μm.

The outer sealing material, on the other hand, may also have an annular shape. The sealing material may then in particular be pushed onto the main body, or rolled into the intended position on the main body. The length of the ring in the axial direction may be equal to or smaller than half its diameter.

Rings may be used having a wall thickness from 10 μm to 1 mm, particularly having a wall thickness from 50 μm to 250 μm.

The outer sealing material may generally also be introduced in another manner. For example, it may be injection-molded onto the main body in the liquid state. A further alternative is to initially bring the outer sealing material into contact with the sealing surface on the housing side, for example by injection molding it into the sealing surface on the housing side.

It is essential for the method according to the present invention to situate the outer sealing material and the main body in the interior of a housing, so that the outer sealing material is situated between the main body and the housing. In particular, hereafter the entire outer seal or only a portion of the outer seal is situated between the main body and the housing.

It is provided in particular that the combination of the main body, the outer sealing material and the housing is heated and caulked at the factory. This results in particular in partial melting of the outer sealing material and subsequently in particular in an integral joint between the housing and the plug, in particular between the housing and the outer seal and/or between the outer seal and the main body of the plug. As an alternative, it is possible that the heating of the combination of the main body, the outer seal and the housing is not carried out at the factory, but in particular not until commissioning of the sensor. Once again, an integral joint may then result between the housing and the plug, in particular between the housing and the outer seal and/or between the outer seal and the main body of the plug.

Heating to 285° C. to 310° C. may be used, moreover it may be that heating to higher temperatures is dispensed with. In particular, heating of the plug to more than 327° C. is dispensed with.

It is provided in particular that the combination of the main body, the sealing material and the housing is caulked by an externally applied pressure of 700 N/cm^2 to 2000 N/cm^2, in particular. The caulking may in particular take place simultaneously with the heating step. In particular, an integral joint between the housing and the plug may be formed during caulking.

Refinements of the manufacturing method according to the present invention result due to the fact that the seal between the main body of the plug and the housing of the exhaust gas sensor is transferred to the seal between the main body of the plug and the connecting line by providing the outer seal according to the present invention.

It may thus be provided that, in addition to the outer seal between the main body of the plug and the housing of the exhaust gas sensor, also the seal described above between the main body of the plug and the connecting line is established. For this purpose, a connecting cable, which includes at least one perfluoroalkoxy polymer or a tetrafluoroethylene-perfluoropropylene or a polychlorotrifluoroethylene or a polyvinylidene fluoride as the sealing material radially on the outside, is led through the axial through-channel of the main body, so that the sealing material ends up in the axial through-channel.

In particular, a combination of the housing, the outer seal, the main body, the sealing material of the seal and the connecting cable is manufactured, and the entire combination is heated together and caulked, in particular by an externally applied pressure of 700 N/cm^2 to 2000 N/cm^2.

It may additionally be provided during this heating that, in addition to the outer sealing material, in particular simultaneously also the sealing material at least partially melts and subsequently an integral joint forms between the main body, the sealing material and the connecting cable.

In particular, it is particularly advantageous when the sealing material to be introduced agrees with the outer sealing material to be introduced with respect to its chemical composition and its handling. For example, the sealing material and the outer sealing material may both be processed in the form of hot-melt films which are 100 μm to 200 μm thick.

Exemplary embodiments of the present invention are shown in the drawings and are described in greater detail in the following description.

DETAILED DESCRIPTION

Figure 1A:
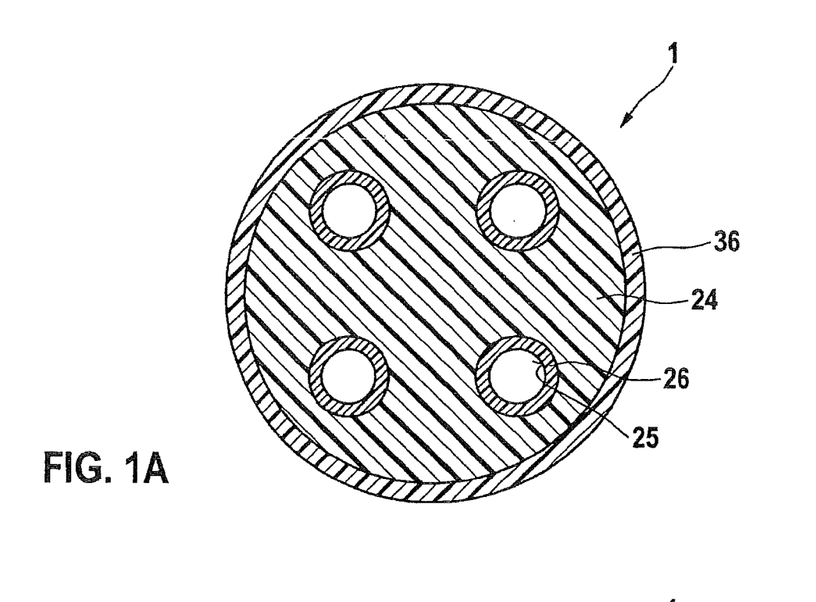
FIGS. 1a and 1b, 2a and 2b, 3a and 3b, and 4a and 4b, in each case, show plugs according to the present invention in top views and along a section along a longitudinal axis of the plug.
Figure 1B:
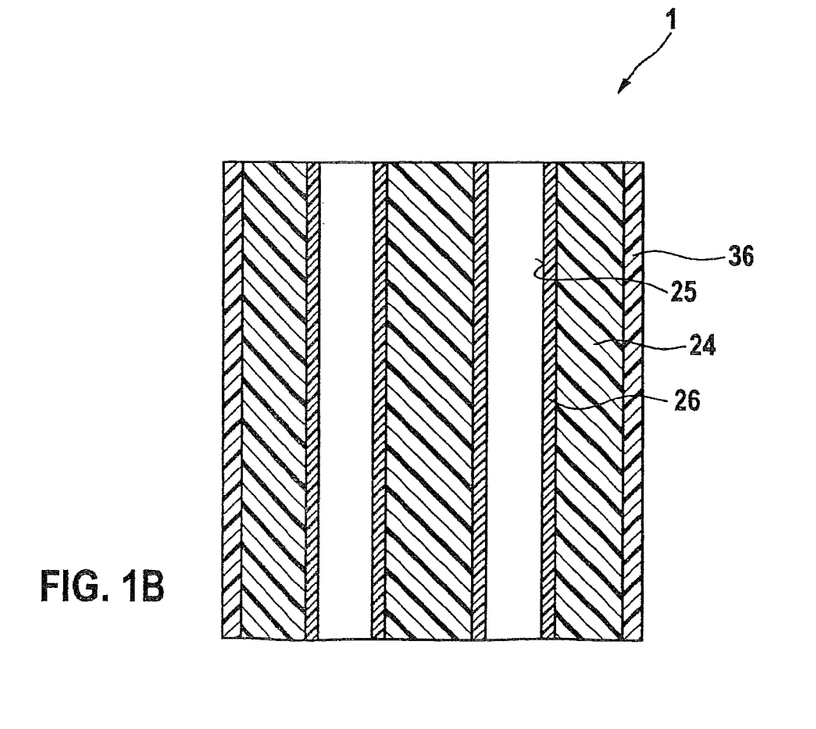

FIGS. 1a and 1b show a first exemplary embodiment of a plug 1 according to the present invention in a top view and in a section along the longitudinal axis of plug 1.

Plug 1 has a cylindrical shape or basic shape, in particular the shape or the basic shape of a straight circular cylinder.

A main body 24 situated radially on the inside also has a cylindrical shape or basic shape, in particular the shape or the basic shape of a straight circular cylinder. For example, main body 24 may have a length of 15 mm and a diameter of 10 mm. Plug 1 or main body 24 has four axial through-channels 25, for example, which extend in the longitudinal direction and have a diameter of 1 mm, for example. Through-channels 25 in this exemplary embodiment of a plug 1 according to the present invention are open and provided for leading through a connecting cable 21 (see FIGS. 3 through 5) in each case. A seal 26 is formed in each case on the inner contours of main body 24, i.e., delimiting through-channels 25 radially to the outside, and in particular across the entire surface in the form of a 100 μm thick layer, for example. An outer seal 36 is applied radially on the outside, to the lateral surface of main body 24, also across the entire surface in the form of a 100 μm thick layer, for example.

In this example, main body 24 is made of polytetrafluoroethylene (PTFE) and accounts for more than 95% of the volume or of the mass of plug 1, resulting in very high thermal stability of plug 1. The material of seal 26 and of outer seal 36 in this example is a perfluoroalkoxy (PFA) polymer in each case, having a melting range from 260° C. to 320° C. As an alternative, the material of seal 26 and of outer seal 36 is one of the following materials: perfluoroalkoxy (PFA) polymer, tetrafluoroethylene-perfluoropropylene (FEP), polychlorotrifluoroethylene (PCTFE), or polyvinylidene fluoride (PVDF). Other materials which only partially include the described materials and/or mixtures of the described materials are also generally possible.

It is provided that a housing 11 of an exhaust gas sensor 2 (see FIG. 5) is sealable with the aid of plug 1 according to the present invention, main body 24 of plug 1 being sealable with respect to a connecting cable 21 with the aid of seal 26, and main body 24 of plug 1 being sealable with respect to housing 11 of exhaust gas sensor 2 with the aid of outer seal 36.

To improve the sealing action of seal 26 or of outer seal 36, it is provided in this example that seal 26 and main body 24 are integrally joined with each other by fusing, and outer seal 36 and main body 24 are integrally joined with each other by fusing. In particular, it is provided that the material of seal 26 or of outer seal 36 melts or partially melts during fusing. In particular, it is provided that the material of main body 24 does not melt, or partially melt, or chemically decompose, during fusing.

Figure 2A:
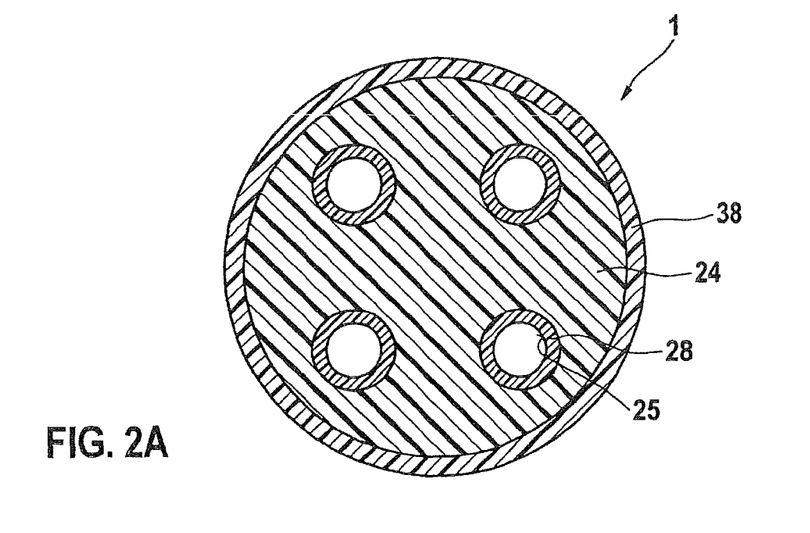
Figure 2B:
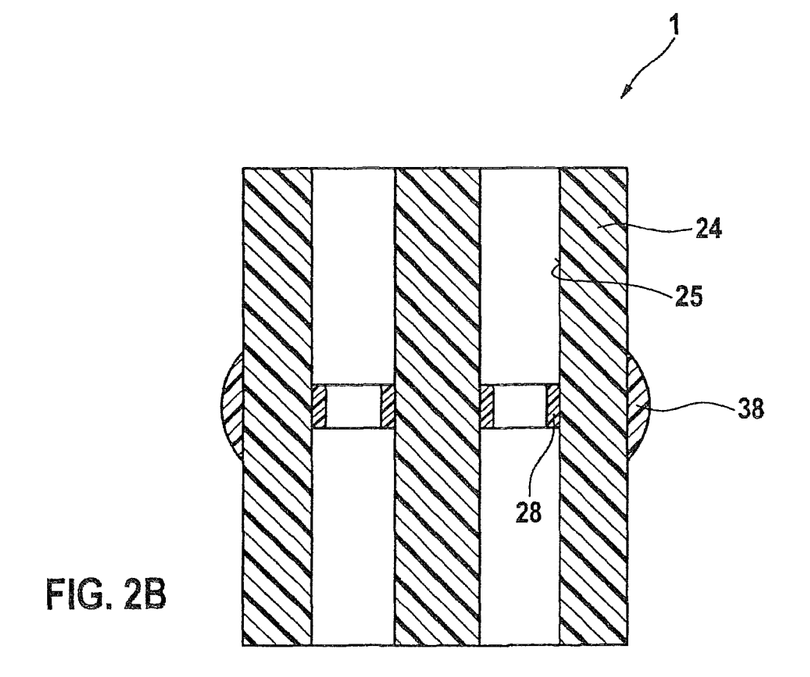

FIGS. 2a and 2b show a second exemplary embodiment of a plug 1 according to the present invention in a top view and in a section along the longitudinal axis of plug 1.

The second exemplary embodiment differs from the first exemplary embodiment in that seal 26 is not configured as a full-surface layer on the inner contour of main body 24, but is situated as a sealing ring 28 on the inner contour of the main body and only partially covers this contour in the longitudinal extension. Sealing ring 28 has a length (longitudinal direction of through-channel 25) of 1 mm and a thickness (radial direction) of 150 μm or 250 μm.

The second exemplary embodiment moreover differs from the first exemplary embodiment in that outer seal 36 is not configured as a full-surface layer radially on the outside on main body 24, but is situated as outer sealing ring 38 radially on the outside on main body 24 and only partially covers the outer surface of main body 24 in the longitudinal extension. Outer sealing ring 38 has a length (longitudinal direction of main body 24) of 3 mm and a thickness (radial direction) of 250 μm or 600 μm.

In this example, sealing ring 28 and outer sealing ring 38 are situated approximately centrally, in particular centrally, in the longitudinal direction of plug 1. In alternatives of the exemplary embodiment, it may also be provided that sealing ring 28 and/or outer sealing ring 38 is/are situated eccentrically. In particular, it is possible to provide two sealing rings 28 and/or two outer sealing rings 38, which are situated opposite each other viewed in the longitudinal direction of plug 1. Generally, it is also possible to provide even more sealing rings 28 and/or outer sealing rings 38.

Figure 3A:
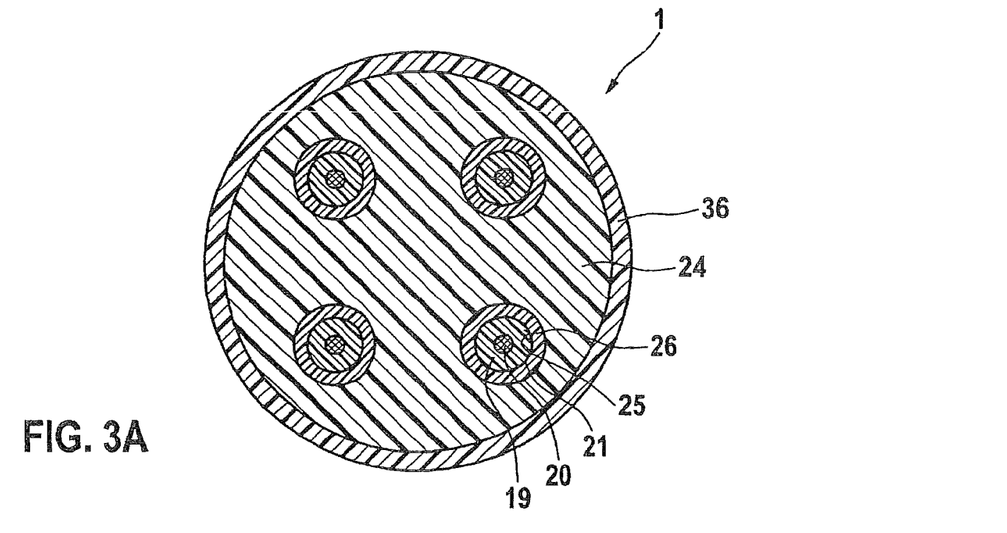
Figure 3B:
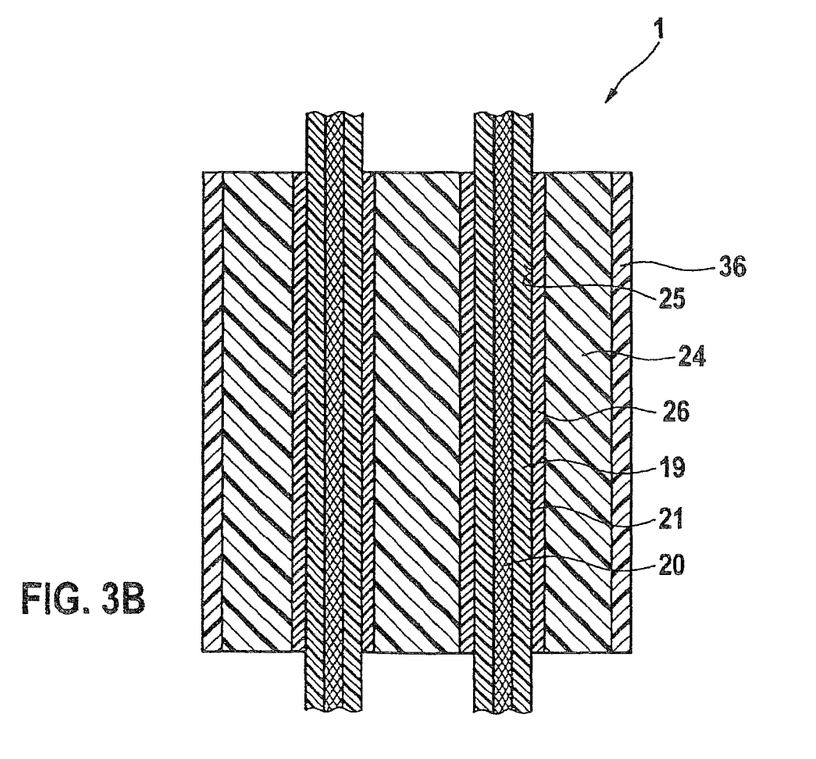

FIGS. 3a and 3b show a third exemplary embodiment of a plug 1 according to the present invention in a top view and in a section along the longitudinal axis of plug 1.

In one refinement of the present invention, for example according to the first or second exemplary embodiment, this involves a plug 1 in which at least one connecting cable 21 is situated in through-channel 25, or through whose through-channel 25 at least one connecting cable 21 is led, so that the plug is in particular suitable for sealing housing 11 of an exhaust gas sensor 2.

Presently, connecting cable 21 is an electrical conductor 20, which is configured in particular as a copper strand or steel-copper strand, electrical conductor 20 in particular being surrounded by an insulation 19, in particular being surrounded by insulation 19 along the entire length of plug 1. As an alternative, it would also be possible that electrical conductor 20 is surrounded by insulation 19 only along a portion of plug 1, and is situated directly opposite seal 26 and/or sealing ring 28 and/or main body 24 of plug 1 along a portion of plug 1.

It may be provided that connecting cable 21, in particular insulation 19, is integrally joined, in particular fused, with seal 26 and/or sealing ring 28, in particular by partially melting the material provided for seal 26 or for sealing ring 28.

However, as an alternative it may also be provided that connecting cable 21, in particular insulation 19, is not integrally joined with seal 26 and/or sealing ring 28, but is only fixed, in particular in a force-fit manner, in the interior of seal 26 and/or sealing ring 28, or in the interior of main body 24. However, in this case it particularly may be that connecting cable 21, in particular insulation 19, is integrally joinable, in particular weldable, with seal 26 and/or sealing ring 28.

Figure 4A:
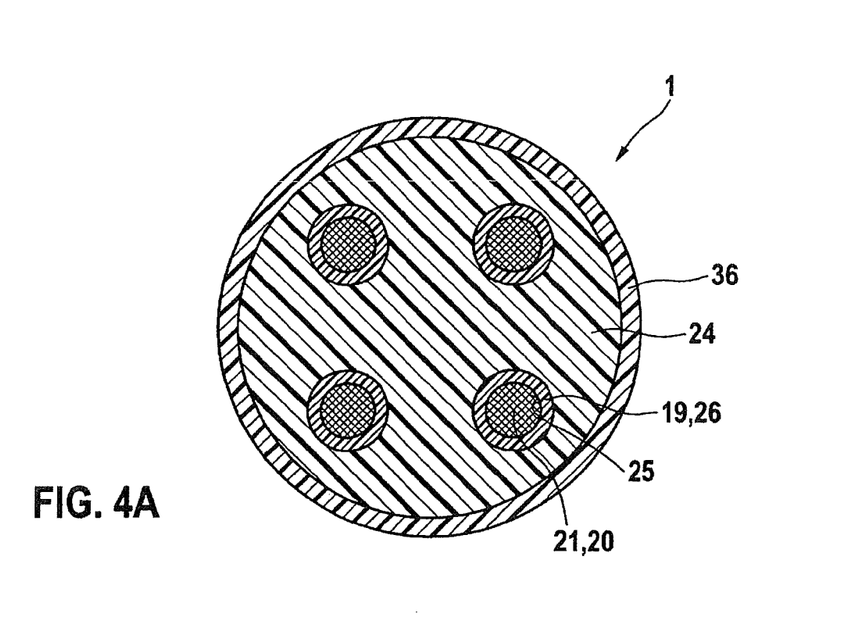
Figure 4B:
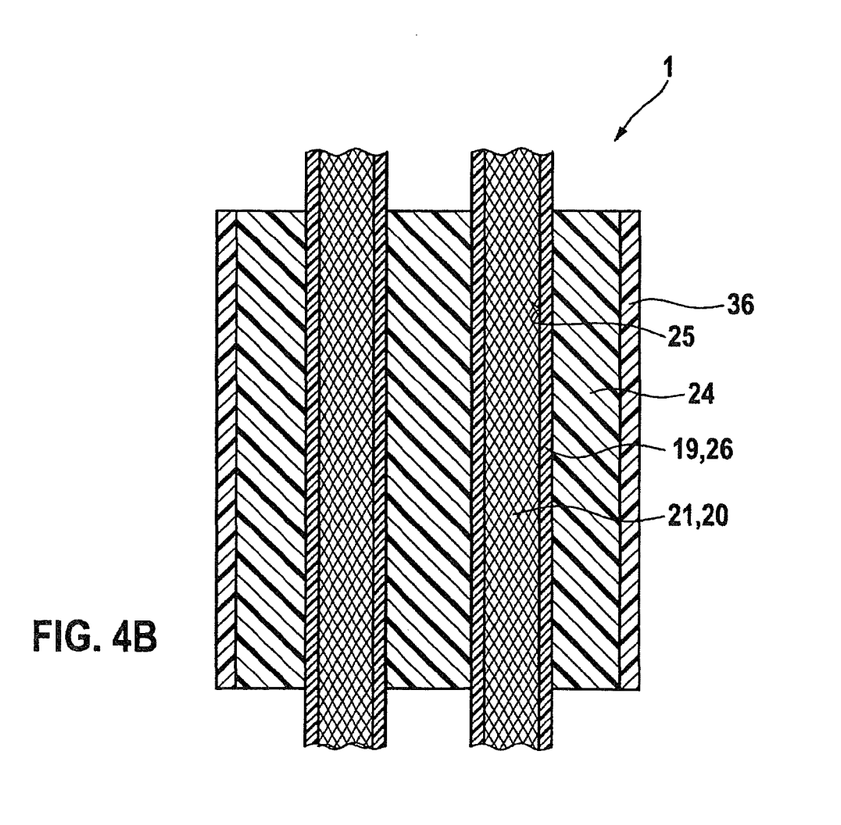

FIGS. 4a and 4b show a fourth exemplary embodiment of a plug 1 according to the present invention in a top view and in a section along the longitudinal axis of plug 1.

In one refinement of the present invention, for example according to the first or second exemplary embodiment, this involves a plug 1 in which at least one connecting cable 21 is situated in through-channel 25, or through whose through-channel 25 at least one connecting cable 21 is led, so that plug 1 is in particular suitable for sealing housing 11 of an exhaust gas sensor 2.

Contrary to the third exemplary embodiment, it is provided that insulation 19 of connecting cable 21 and seal 26 are not configured as different parts, but seal 26 at the same time assumes the function of insulation 19 of electrical conductor 20 and is situated, in particular directly, opposite of the same. In this example, seal 26 or insulation 19 is led out of plug 1 together with electrical conductor 20, in particular on two sides or on one side, and also insulates electrical conductor 20 of connecting cable 21 outside plug 1, for example up to a part (not shown) of a plug connection, for example a connector, which is connected to connecting cable 21 on the side of connecting cable 21 situated opposite plug 1 and which is connectable to, in particular pluggable into, a complementary part of the plug connection which forms part of a control unit, for example a jack.

In this example, insulation 19, which within plug 1 at the same time forms insulation 26, is configured as a 250 μm thick layer made of perfluoroalkoxy (PFA) polymer, which surrounds the electrical conductor radially on the outside in the form of an insulating tube.

In this example, it may be provided that insulation 19, i.e., presently seal 26, is integrally joined, in particular fused, with conductor 20 of connecting cable 21 and/or with main body 24 of plug 1, in particular by partially melting the material provided for insulation 19, i.e., presently for seal 26.

However, as an alternative it may also be provided that insulation 19, i.e., presently seal 26, is not integrally joined with conductor 20 of connecting cable 21 and/or with main body 24 of plug 1, but that insulation 19, i.e., presently seal 26, is merely fixed, in particular in a force-fit manner, to conductor 20 of connecting cable 21 and/or to main body 24 of plug 1. However, in this case it particularly may be that insulation 19, i.e., presently seal 26, is integrally joinable, in particular weldable, with conductor 20 of connecting cable 21 and/or with main body 24 of plug 1.

In alternatives of the exemplary embodiment it may also be provided that insulation 19, which within plug 1 at the same time forms insulation 26, is not made of perfluoroalkoxy (PFA) polymer, but is made of a material which includes at least one perfluoroalkoxy (PFA) polymer or a tetrafluoroethylene-perfluoropropylene (FEP) or a polychlorotrifluoroethylene (PCTFE) or a polyvinylidene fluoride (PVDF), in particular such a material which is electrically insulating and is temperature-resistant up to or above 190° C.

The fourth exemplary embodiment is in particular also an exemplary embodiment for a plug 1 for sealing housing 11 of an exhaust gas sensor 2, plug 1 having a main body 24 which includes polytetrafluoroethylene, plug 1 having at least one axial through-channel 25 through which an electrical conductor 20 is led, an insulating seal 26 being situated at least in places between main body 24 of plug 1 and through-channel 25, the seal being led out of plug 1 together with electrical conductor 20 on at least one side, i.e., in particular on an end face of plug 1, insulating seal 26 including at least one perfluoroalkoxy polymer or a tetrafluoroethylene-perfluoropropylene or a polychlorotrifluoroethylene or a polyvinylidene fluoride. Insulating seal 26 here is situated in particular directly opposite electrical conductor 20 and main body 24, and in particular is joined or joinable, in particular integrally, in particular welded or weldable, with electrical conductor 20 and/or to main body 24, in particular within through-channel 25.

Further exemplary embodiments of the present invention relate to exhaust gas sensors 2 having a plug 1, for example, as it is described in greater detail above, in particular in the first, second, third and fourth exemplary embodiments. Each of these exhaust gas sensors 2 includes at least one housing 11, which is sealed by plug 1, and at least one connecting cable 21, which is led through through-channel 25 of plug 1.

Figure 5:
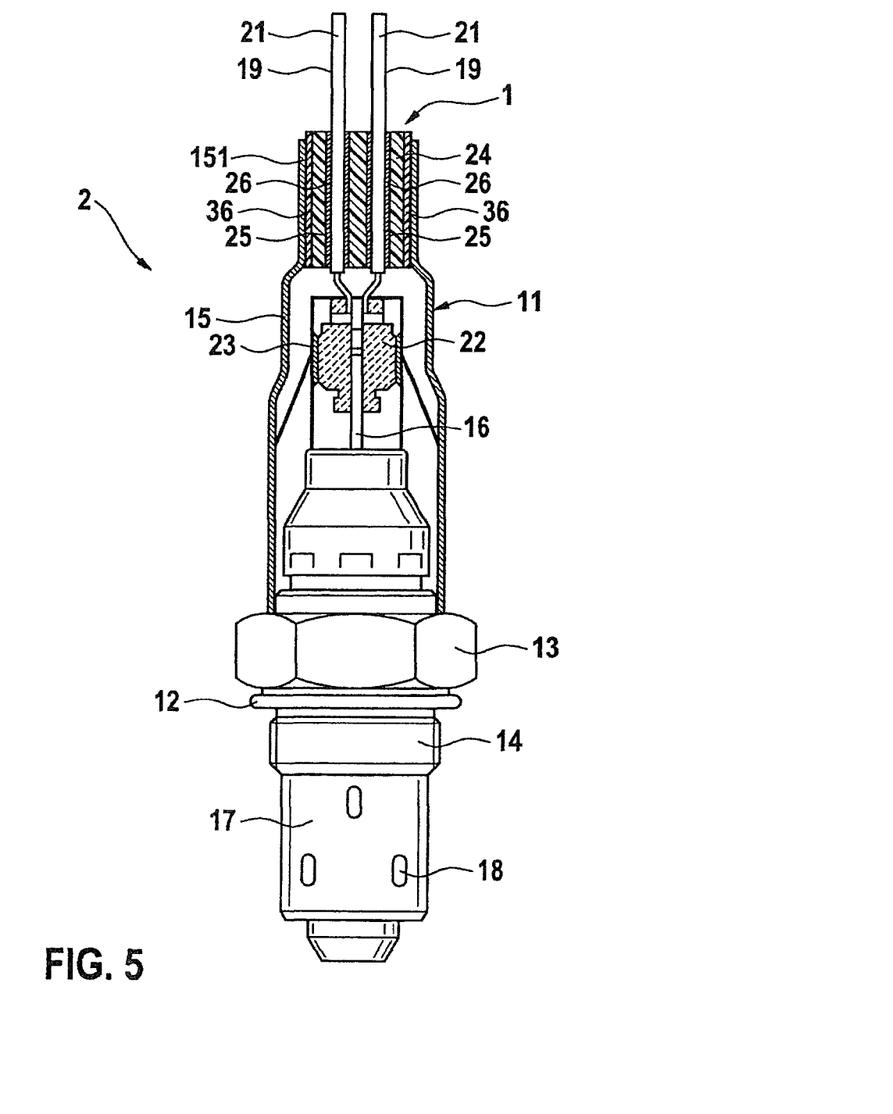
FIG. 5 shows an exhaust gas sensor according to the present invention.

A further exemplary embodiment of the present invention shown in FIG. 5 is an exhaust gas sensor 2 whose portion situated on the exhaust gas side of plug 1 is basically known from the related art and is configured, for example, as part of a lambda sensor for measuring the oxygen concentration in the exhaust gas of internal combustion engines. This exhaust gas sensor 2 includes a housing 11, which is composed of a solid metal housing body 12, having a screw thread 14 and a mounting hexagon 13, and a protective sleeve 15, which is pushed onto housing body 12 and fixedly connected thereto and has an end section 151 which is remote from the housing body and whose diameter is reduced, for example. For example, a sensor element 16 is situated in housing 11 and protrudes with a measuring gas-side end from housing 11 and is covered there by a protective tube 17, which has gas passage holes 18 and is attached to housing body 12. At the connection-side end facing away from the measuring gas-side end, sensor element 16 has contact surfaces which are connected to measuring electrodes situated on the measuring gas-side end via conductors. Electrical conductors 20 of connecting cables 21, which are surrounded by an insulation 19, for example, are contacted with the contact surfaces. In this exemplary embodiment, a two-part, ceramic clamping body 22 is provided for contacting contact surfaces and electrical conductors 20, the clamping body being surrounded on the outside by a spring element 23 and pressing electrical conductors 20 onto the contact surfaces of sensor element 16 in a force-fit manner. Ceramic clamping body 22 is radially supported on protective sleeve 15.

Alternatives of this portion of an exhaust gas sensor 2, which is described by way of example and situated on the exhaust gas side of a plug 1, are also generally possible and/or also known from the related art.

It is provided in the further exemplary embodiments that plug 1 closes or seals housing 11 by being situated in the portion of protective sleeve 15 facing away from housing body 12, in particular in an end section 151 of protective sleeve 15 remote from the housing body.

As is shown in FIG. 5, for example, plug 1 may be plug 1 described in connection with the third exemplary embodiment of the present invention (FIG. 3). As an alternative, it may also be a plug 1 as it was described in connection with the first, second and/or fourth exemplary embodiment(s) (FIGS. 1, 2 and 4).

It may be provided in the further exemplary embodiments that outer seal 36 is integrally joined, in particular fused, with main body 24 of plug 1 and/or with housing 11, in particular with protective sleeve 15 and/or end section 151 of protective sleeve 15 remote from the housing body, in particular by partially melting the material provided for outer seal 36.

However, as an alternative, it may also be provided in the further exemplary embodiments that outer seal 36 is not integrally joined with main body 24 of plug 1 and/or with housing 11, in particular with protective sleeve 15 and/or with end section 151 of protective sleeve 15 remote from the housing body, but that outer seal 36 is merely fixed, in particular in a force-fit manner, to main body 24 of plug 1 and/or to housing 11, in particular to protective sleeve 15 and/or to end section 151 of protective sleeve 15 remote from the housing body. However, in this case it particularly may be that outer seal 36 is integrally joinable, in particular weldable, with main body 24 of plug 1 and/or with housing 11, in particular with protective sleeve 15 and/or end section 151 of protective sleeve 15 remote from the housing body.

One exemplary embodiment of the method according to the present invention for manufacturing an exhaust gas sensor 2 provides for a main body 24 including polytetrafluoroethylene and having at least one axial through-channel 25 to be provided, and for a connecting cable, which radially on the outside includes a sealing material, for example in the form of a 150 μm thick film, which includes at least one perfluoroalkoxy polymer or a tetrafluoroethylene-perfluoropropylene or a polychlorotrifluoroethylene or a polyvinylidene fluoride, to be led through through-channel 25. It is furthermore provided that this combination of main body 24 and connecting cable 21, together with an outer sealing material, for example a 150 μm thick film, which includes at least one perfluoroalkoxy polymer or a tetrafluoroethylene-perfluoropropylene or a polychlorotrifluoroethylene or a polyvinylidene fluoride, is situated in the interior of a housing 11, so that the outer sealing material is situated between main body 24 and housing 11. In this example, it is provided that the arrangement takes place in an end section 151 of a protective sleeve 15 which is remote from the housing body, the sleeve being mountable with a housing body 12 to form a housing 11.

It is provided in particular that, in particular overall, an integral seal of housing 11 or of protective sleeve 15 is created by caulking and heating of the combination of connecting cable 21, sealing material, main body 24, outer sealing material and housing 11 and protective sleeve 15. In particular, fusion takes place by partially melting the sealing material and the outer sealing material.

In the example, the caulking is carried out at an applied pressure of 700 N/cm^2 to 2000 N/cm^2. The combination of connecting cable 21, sealing material, main body 24, outer sealing material and housing 11 may be heated over a time period of 10 seconds or more, which may be 30 seconds or more, so that melting of the sealing material and of the outer sealing material takes place reliably.

It is further provided in this example that the heating takes place up to a temperature which is above the melting temperature of the sealing material or of the outer sealing material, i.e., for example above 280° C. for perfluoroalkoxy (PFA) polymer, above 240° C. for tetrafluoroethylene-perfluoropropylene (FEP), above 190° C. for polychlorotrifluoroethylene (PCTFE), above 170° C. for polyvinylidene fluoride (PVDF), so that melting of the sealing material and of the outer sealing material takes place reliably. Particular attention during heating must be directed to ensuring that the heating is carried out in such a way that the temperature of the main body does not exceed 327° C. In this way, chemical decomposition of the main body and thus, in particular irreversible, damage to plug 1, are reliably prevented.

What is claimed is:

1. A plug for sealing a housing of an exhaust gas sensor, comprising:
at least one axial through-channel for leading through a connecting cable;
a main body which includes polytetrafluoroethylene; and
at least one outer seal situated on the plug radially on the outside of the main body, wherein the at least one outer seal includes at least one of perfluoroalkoxy polymer, tetrafluoroethylene-perfluoropropylene, polychlorotrifluoroethylene, and polyvinylidene fluoride.

2. The plug of claim 1, wherein the main body is integrally joined with the at least one outer seal.

3. The plug of claim 1, wherein the at least one outer seal is situated on the main body in the form of a layer having a layer thickness of 10 μm to 1 mm.

4. The plug of claim 1, wherein the at least one outer seal is situated on the main body in the form of a layer having a layer thickness of 50 μm to 250 μm.

5. An exhaust gas sensor, comprising:
a plug for sealing a housing of the exhaust gas sensor, including:
at least one axial through-channel for leading through a connecting cable;
a main body which includes polytetrafluoroethylene; and at least one outer seal situated on the plug radially on the outside of the main body, wherein the at least one outer seal includes at least one of perfluoroalkoxy polymer, tetrafluoroethylene-perfluoropropylene, polychlorotrifluoroethylene, and polyvinylidene fluoride;

a housing; and at least one connecting cable, which is led through the at least one axial through-channel of the plug, wherein the housing of the exhaust gas sensor is sealed by the plug.

6. The exhaust gas sensor of claim 5, wherein the housing of the exhaust gas sensor is indirectly integrally joined with the plug via the at least one outer seal.

7. The exhaust gas sensor of claim 5, wherein the at least one connecting cable, the at least one outer seal and the main body are integrally joined with each other at least indirectly.

8. The exhaust gas sensor of claim 5, wherein the at least one connecting cable includes an electrical conductor surrounded by an insulation, which includes a fluoropolymer.

9. The exhaust gas sensor of claim 5, wherein the at least one connecting cable, the plug and the housing are integrally joined with each other at least indirectly.

10. The exhaust gas sensor of claim 5, wherein the at least one connecting cable includes an electrical conductor surrounded by an insulation, which includes a polytetrafluoroethylene.

11. A method for manufacturing an exhaust gas sensor, the method comprising:

providing a main body including polytetrafluoroethylene;

providing an outer sealing material including at least one of perfluoroalkoxy polymer, tetrafluoroethylene-perfluoropropylene, polychlorotrifluoroethylene, and a polyvinylidene fluoride;

situating the outer sealing material and the main body in the interior of a housing so that the outer sealing material is situated between the main body and the housing;

caulking and heating the outer combination of the main body, the outer sealing material and the housing to form in particular an overall at least indirectly integral structure;

wherein the exhaust gas sensor, includes:

a plug for sealing the housing of the exhaust gas sensor, including:

at least one axial through-channel for leading through a connecting cable;

a main body which includes polytetrafluoroethylene;

the outer sealing material situated on the plug radially on the outside of the main body;

the housing; and at least one connecting cable, which is led through the at least one axial through-channel of the plug, wherein the housing of the exhaust gas sensor is sealed by the plug.

12. The method of claim 11, wherein the outer sealing material is provided by injection molding it onto the main body.

13. The method of claim 11, wherein the outer sealing material is provided in the form of at least one tube, at least one film, and/or at least one ring.

14. The method of claim 11, wherein the caulking takes place at an externally applied pressure of 700 N/cm$^2$ to 2000 N/cm$^2$.

15. The method of claim 11, wherein the heating is carried out in such a way that the outer sealing material at least partially melts and, at least indirectly, an integral joint forms between the main body, the outer sealing material and the housing.

16. The method of claim 11, wherein the heating is carried out so that the temperature of the main body does not exceed 327° C.

* * * * *